United States Patent [19]
Jinotti

[11] Patent Number: 5,140,983
[45] Date of Patent: Aug. 25, 1992

[54] MULTI PURPOSE CATHETER ASSEMBLY

[76] Inventor: Walter J. Jinotti, 10 Scott St., New Brunswic, N.J. 08903

[21] Appl. No.: 571,709

[22] Filed: Aug. 24, 1990

Related U.S. Application Data

[63] Continuation-in-part of Ser. No. 507,477, Apr. 11, 1990.

[51] Int. Cl.⁵ .................. A61M 16/00; A61M 25/00; A62B 9/06
[52] U.S. Cl. .................. 128/207.14; 128/205.24; 128/911; 604/267; 604/905
[58] Field of Search ............... 128/207.14, 200.24, 128/911, 912, DIG. 26, 205.24; 604/267, 905

[56] References Cited

U.S. PATENT DOCUMENTS

| | | | |
|---|---|---|---|
| 3,991,762 | 11/1976 | Radford | 128/351 |
| 4,193,406 | 3/1980 | Jinotti | 128/204.18 |
| 4,354,490 | 10/1982 | Rogers | 128/213 A |
| 4,416,273 | 11/1983 | Grimes | 128/207.16 |
| 4,432,759 | 2/1984 | Gross et al. | 604/411 |
| 4,517,979 | 5/1985 | Pecenka | 128/325 |
| 4,545,367 | 10/1985 | Jucci | 128/344 |
| 4,551,146 | 11/1985 | Rogers | 604/403 |
| 4,585,440 | 4/1986 | Tchervenkov et al. | 604/164 |
| 4,595,005 | 6/1986 | Jinotti | 128/205.24 |
| 4,610,469 | 9/1986 | Wolff-Mooij | 285/260 |
| 4,655,762 | 4/1987 | Rogers | 604/403 |
| 4,810,241 | 3/1989 | Rogers | 604/28 |
| 4,935,010 | 6/1990 | Cox et al. | 604/122 |
| 4,995,386 | 2/1991 | Ng | 128/205.19 |
| 4,995,387 | 2/1991 | Jinotti | 128/205.24 |

*Primary Examiner*—Edgar S. Burr
*Assistant Examiner*—Kimberly L. Asher
*Attorney, Agent, or Firm*—Robert A. Green

[57] ABSTRACT

The disclosure is of a catheter assembly including a hollow T-shaped member having a patient end and a rear end which is blocked from the patient end by a wall. A catheter is adapted to be introduced through the rear end of the member into a patient and the rear end includes a sponge, located out of the airway of the patient by the wall but the wall includes means for opening the wall to let the catheter through it for introduction into the patient. The sponge cleans the catheter as it is withdrawn but mucus cannot be returned to the airway to the patient.

16 Claims, 5 Drawing Sheets

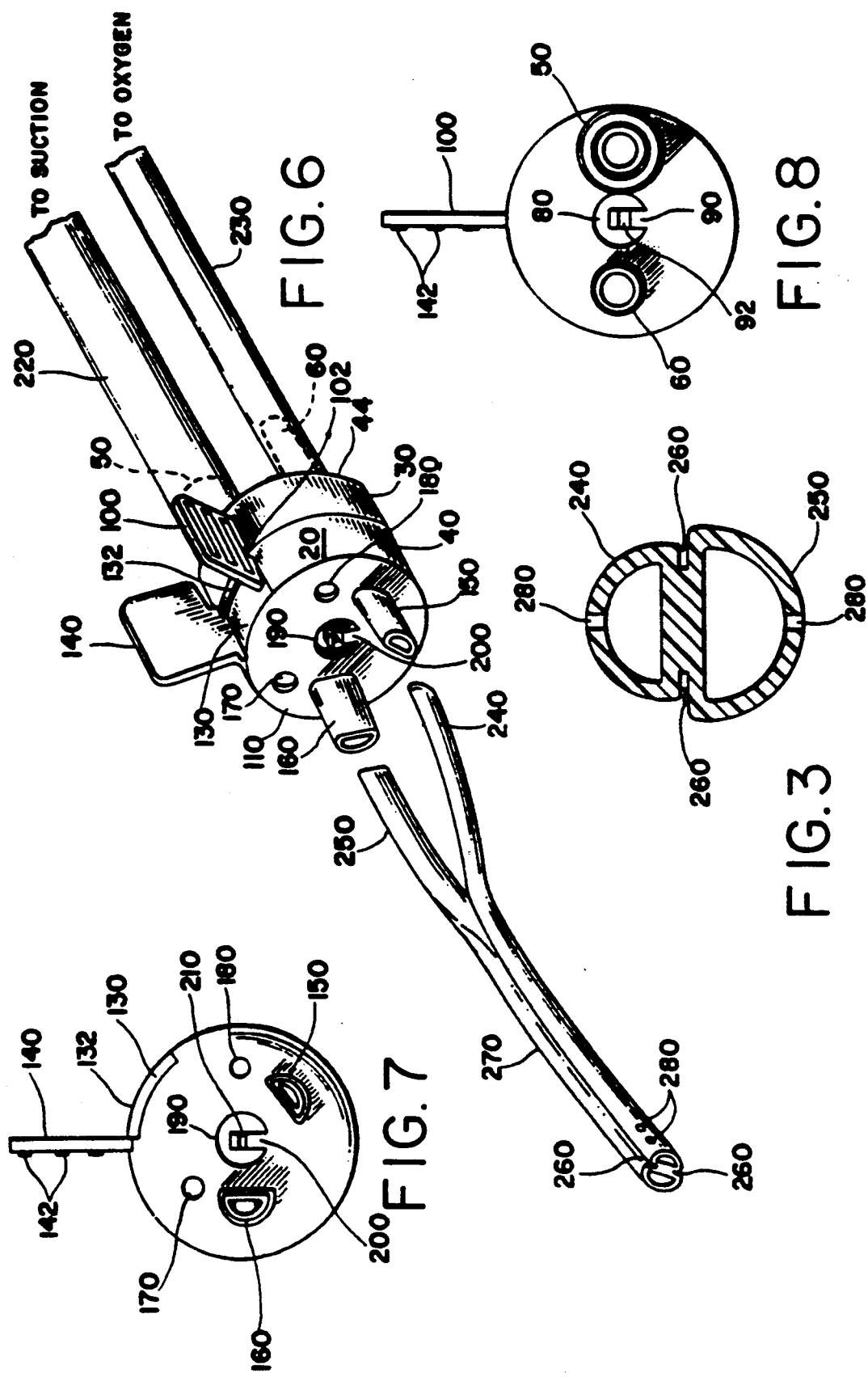

MULTI PURPOSE CATHETER ASSEMBLY

CROSS REFERENCE TO RELATED APPLICATIONS

This application is a continuation-in-part of application Ser. No. 07/507,477 filed Apr. 11, 1990.

BACKGROUND OF THE INVENTION

One type of system used for applying oxygen and suction to a patient, for example during or after surgery, uses a T shaped connector through which a catheter is introduced through the patient's mouth into the lungs.

In one known apparatus for performing the above-described operation using a catheter with a T connector, the catheter tube or lumen is fed through a sponge or the like into the T connector and then into the patient. The sponge is directly in one of the branches of the T connector and when the catheter is withdrawn through the sponge, mucus is trapped on the sponge in the passageway into the patient and thus can be drawn into the patient's lungs. This is a dangerous situation for the patient.

In addition, the prior art does not show a suctioning and oxygenating system which is a closed system which can prevent a patient from suffering oxygen depletion.

SUMMARY OF THE INVENTION

The above-described problems or failings in the prior art are solved by the present invention by means of a combination catheter and T connector wherein the sponge through which the catheter is drawn is not within the T connector but is in a chamber removed from the passageway and any mucus retained thereon cannot be drawn back into the patient. In addition, the system of the invention includes means which renders it a closed system which prevents a patient from suffering oxygen depletion during use.

DESCRIPTION OF THE DRAWINGS

FIG. 3 is a sectional view along the lines 3—3 in FIG. 1;

FIG. 6 is a perspective view of the catheter and valve used in practicing the invention;

FIG. 7 is a front elevational view of the valve of FIG. and 6;

FIG. 8 is a rear elevational view of the valve of FIG. and 6;

DESCRIPTION OF THE INVENTION

Figure 1:
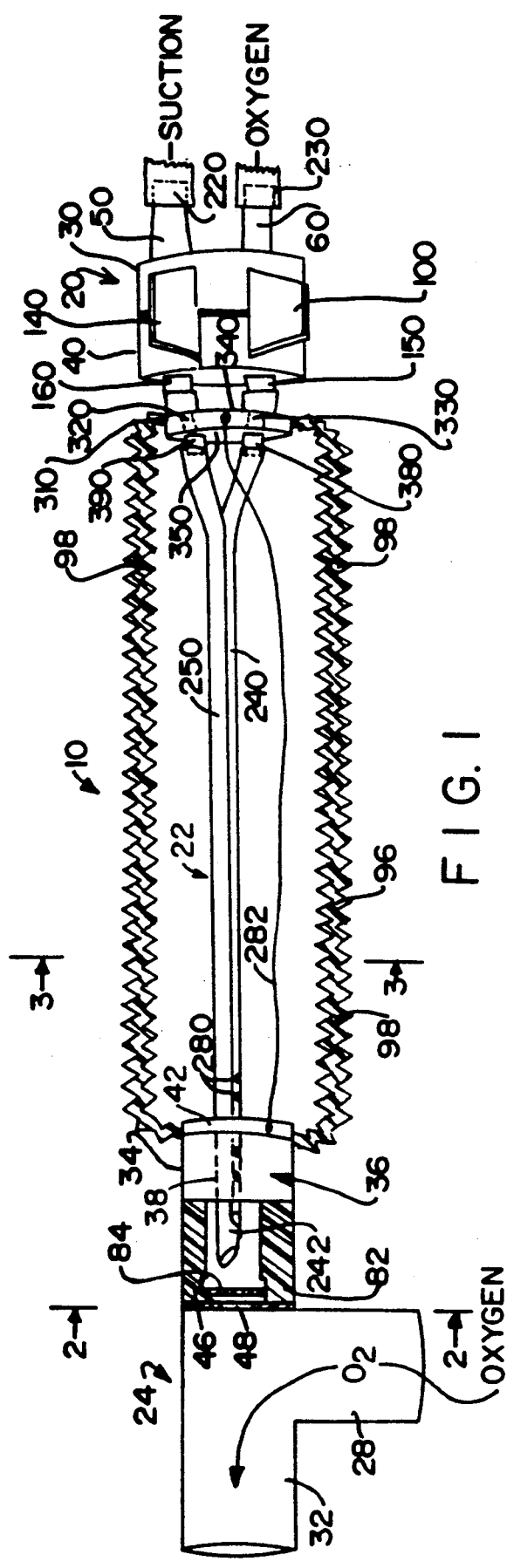
FIG. 1 is a side elevational view of apparatus embodying the invention.

A catheter assembly 10 embodying the invention, referring to FIG. 1, includes a dual-purpose catheter assembly of the type described and claimed in U.S. Pat. No. 4,595,005 and incorporated herein by reference.

The catheter assembly shown in the patent includes a double lumen unit 22, having flexible plastic tubes or lumens 240 and 250 secured together for most of their lengths, one being used to supply oxygen and one being used to provide suction. The flexible lumen tubes preferably have different diameters and shapes to insure proper connections to associated apparatus and in one form they have a cross-section as shown in FIG. 3.

The patient end 242 of the suction tube 250 is open and may have auxiliary holes not shown. The oxygen tube 240 may be open at its patient end and also includes auxiliary holes 280 along its patient end.

The lumen tubes 240 and 250 are connected at one end to a valve 20 for permitting the application of oxygen and suction to a patient as described in the above-identified patent.

It is understood that other catheter assemblies may be used in practising the present invention and this will be appreciated by those skilled in the art.

According to the invention, the catheter is used with a hollow, generally T shaped connector 24 which is a tubular member, preferably of plastic, having a cross member 26 (shown oriented horizontally in FIG. 1) which represents the cross-bar of the T and has a front or patient end 32 which is adapted to be placed in a patient's mouth. The other end or rear end 34 of the cross member carries within it a dry or wet sponge 36 of suitable size which is adapted to clean the end of the catheter lumen unit 22 as the lumen unit is withdrawn from a patient. The sponge 36 has a through-hole 38 through which the catheter lumen assembly 22 of flexible tubes 240 and 250 is pushed into the patient. Preferably, the hole 38 in the sponge matches the size and shape of the catheter lumen unit as shown in FIG. 3.

A removable cap 42 is coupled to the rear end of the connector 24 to permit the sponge 36 to be removed and cleaned or replaced.

The T connector 24 also includes an arm 28 which extends downwardly from the cross portion and this arm is adapted to be coupled to a source of oxygen to be introduced into the patient. The arm 28 may or may not be at 90 degrees to the cross member 26 so that the connector 24 need not be exactly T shaped.

According to the invention, a wall 46 is provided in the cross member in the vicinity of the juncture of the arm 28 but on the side thereof closer to the rear end of the cross member and this wall 46 blocks the portion of the cross member behind it from the patient and the airway to the patient. The wall 46 has a generally central aperture 48.

A hollow tubular sleeve 82 is also provided in the rear portion of the connector 24. The sleeve 82, which may be of plastic, has its rear end bearing against the front end of the sponge 36 to hold the sponge in place and its front end bears against the rear surface of the wall 46. The sleeve 82 does not obstruct opening 48 in the wall 46.

Figure 2:
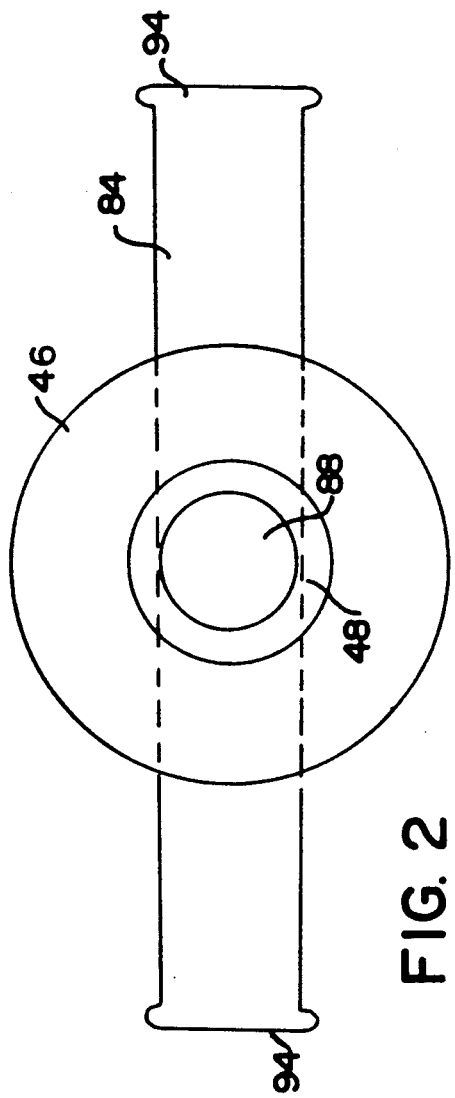
FIG. 2 is a sectional view along the lines 2—2 in FIG. 1.
Figure 4:
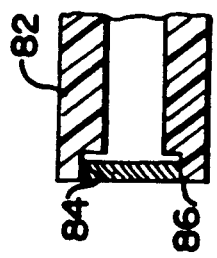
FIG. 4 is a sectional view along the lines 4—4 in FIG. 1.

Means is provided in the wall 46 for permitting the end 242 of the catheter lumen unit 22 to pass through and be directed into the patient. In addition, means is provided to block and unblock the opening 48 in the wall 46. This means, in one embodiment shown in FIGS. 1 and 2, includes a solid slide plate 84 seated behind the wall 46 in the rear portion or rear chamber of the connector 24 and slidable in guides formed on the rear surface of the wall 46 or in guide depressions 86 formed in the front end of the sleeve 82 as seen in FIG.

4. The slide plate 84 includes an aperture 88 and it extends through the wall of the connector to provide external portions 94 by means of which the slide can be manipulated so that its aperture 88 can be aligned with the aperture 48 in the wall 46 or it can be manipulated so that the solid portion of the slide blocks the opening 48. With the opening 88 in the slide plate 84 aligned with the opening 48 in the wall 46, the catheter lumen unit 22 can pass through the aligned openings into the front portion of the T connector and into the patient.

The plate 84 may also be mounted to rotate to achieve the desired blocking and unblocking of aperture 48.

An accordion sleeve or covering 96 is provided coupled to the rear end of the cross arm 26 of the connector 24 and enclosing the length of the catheter lumen unit 22 with its rear end connected to the valve 20 or to associated apparatus. The sleeve 96 includes a plurality of vent holes 98. The covering 96 provides a protective enclosure and may take any suitable form other than accordion.

In using the apparatus of the invention, the front or patient end of the T connector 24 is placed in the patient's mouth and the catheter lumen unit 22 is pushed through the sponge 36 into the aligned openings 48 and 88 in the wall 46 and slide plate 84, respectively, and through the remainder of the cross member 26 and into the patient. During this time, oxygen is fed through arm 28 and the front portion of the connector 24 into the patient. After the required procedure of oxygenating and suctioning the patient has been performed, the catheter is withdrawn and it proceeds through the opening 48 in the wall 46 without any mucus which may be on it being deposited on the wall 46. The opening 48 is closed by suitably sliding the slide plate 84 and then as the catheter passes through the sponge 36, it is cleaned of mucus and other matter. Since, the mucus, if any, is located in a closed compartment of the connector 24 which is sealed off from the patient by wall 46, there is no way by which mucus can be drawn back into the patient.

It is noted that some of the vent holes 280 at the patient end of the oxygen tube 240 lie outside the T connector and within the sleeve 96 so that oxygen can be vented when it is not being fed to a patient.

Figure 5:
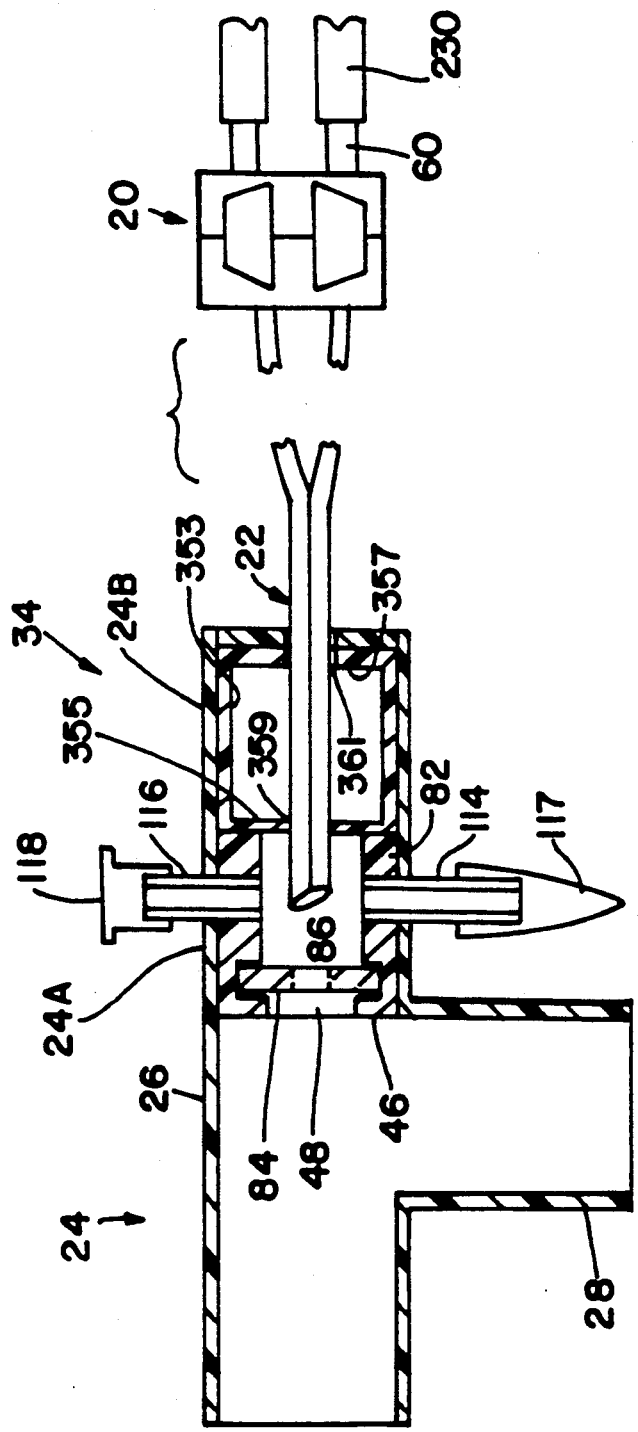
FIG. 5 is a side elevational view of a modification of a portion of the apparatus shown in FIG. 1.

In a modification of the invention, referring to FIG. 5, consider that the rear end 34 of the T connector 24 includes a portion 24A behind wall 46 containing the sleeve 82 and a rearward portion 24B containing the sponge 36. According to this modification of the invention, a first short tube 114 is provided in the wall of the portion 24A extending from inside portion 24A to outside the T connector. The tube is generally vertically oriented. In addition, a second similar tube 116 is provided in the wall of the portion 24A and extending from inside portion 24A to the outside thereof. The tube 116 is generally vertically oriented and may be aligned with tube 114. The outer end of tube 114 has a removable cap 117 and the outer end of tube 116 has a removable cap 118.

In using the portion of the apparatus shown in FIG. 5, the tube 114 can be used to connect suction for cleaning out the T connector. While suction is applied, the tube 116 is held open as a vent. The tube 116 can also be held open as a vent when oxygen is fed into the valve from the oxygen source but it is not applied to the patient.

Figure 9:
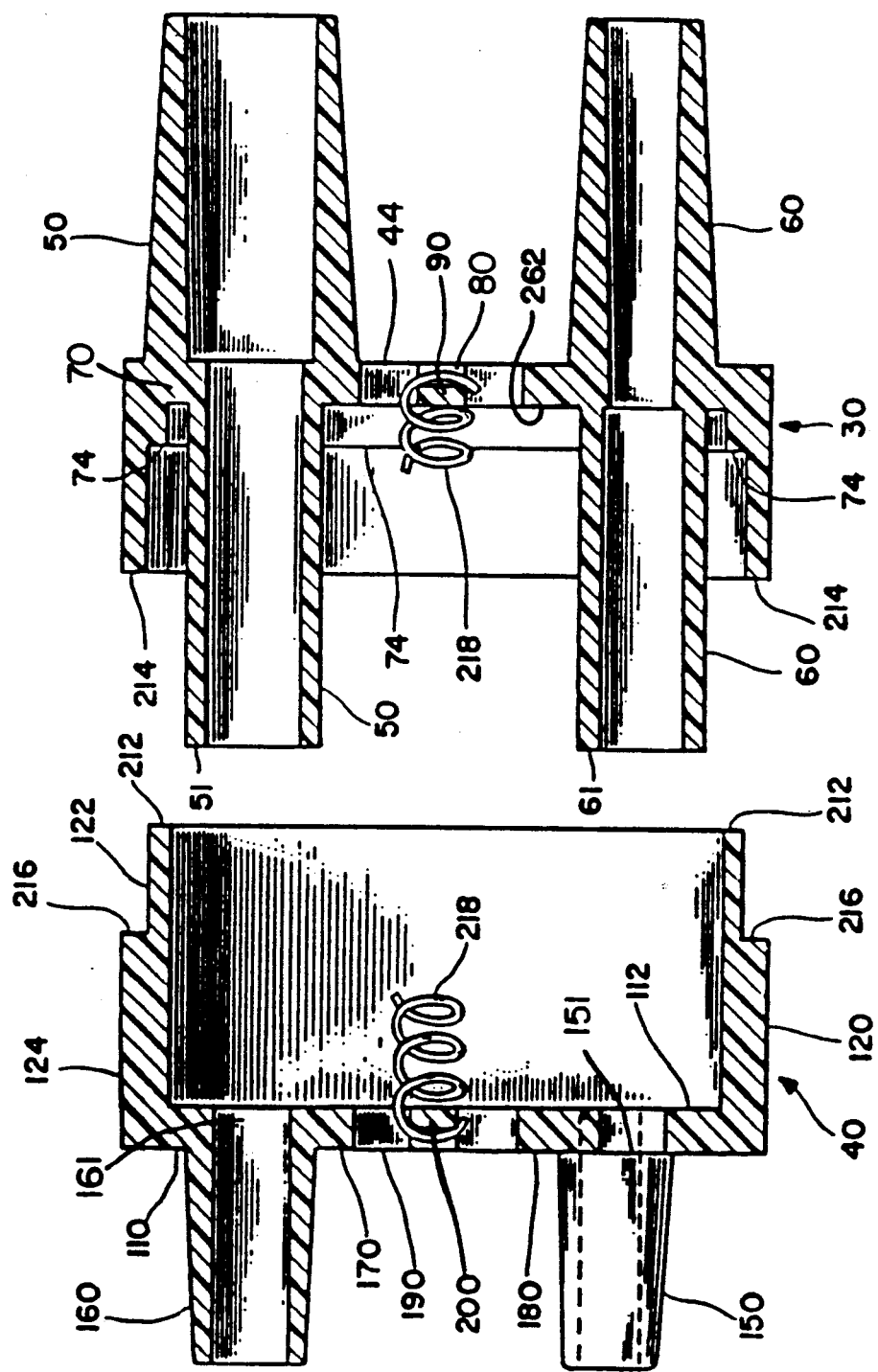
FIG. 9 is a sectional exploded view of the valve shown in FIGS. 1 and 6.
Figure 10:
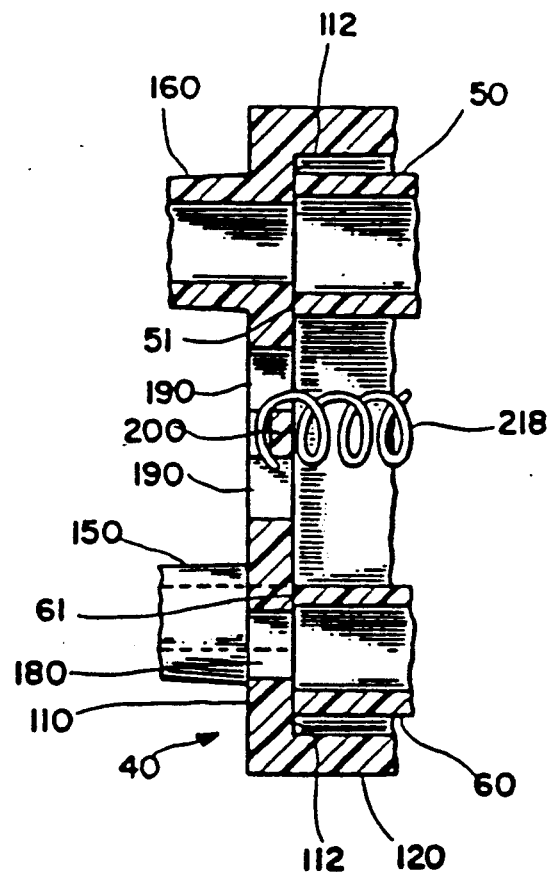
FIG. 10 is a side elevational view of a portion of the valve parts shown in FIG. 9 but assembled.

According to the invention, referring to FIGS. 8 to 10, in order to render the apparatus described above a closed system as far as the patient is concerned so that oxygen cannot be lost by the patient through the catheter lumen unit, and valve 20 the catheter lumen unit is used with a valve mechanism 20 which is similar to that shown in the above-identified patent but embodies novel features not shown in the patent.

The valve 20 comprises two cylindrical bodies 30 and 40 having circular cross-sections and rotatably coupled together. One body 30 includes a flat rear wall 44, through which first and second integral tubes 50 and 60 extend so that the two tubes lie inside and outside the body and thus inside the valve 20 when it is assembled. The inner ends 51 and 61 of tubes 50 and 60 are as smooth as possible for a purpose to be described. Tube 50 is used for connection to a suction source and tube 60 for connection to an oxygen supply, and the suction tube 50 is preferably of larger diameter. A portion 70 of the inner wall of the body 30 (FIG. 8) near rear wall 44 is thickened or is of reduced inside diameter to provide an annular ledge 74 which acts as a stop for the leading end of body 40 when the two are assembled. The rear wall 44 of the body 30 also has a central hole 80 and a notched tab 90 which is formed integral with the body 30 and extends partly across the hole 80. The tab 90 has a notch or depression 92 across its outer surface.

An operating finger tab 100 extends generally perpendicularly from the outer surface of the body 30 for manipulation by the operator of the catheter. The lower edge of tab 100 has a notch 102 for a purpose to be described.

The second body 40 includes a rear wall 110, whose inner surface 112 is as smooth as possible, for a purpose to be described. The annular outer wall 120 of body 40 has a portion 122 of reduced thickness or smaller outside diameter at its leading end for insertion into body 30. Also, the outer surface of the thicker portion 124 is provided with a region 130 of reduced thickness (FIG. 5) having a ledge 132 (FIGS. 5 and 6) where it joins the portion 122 of reduced thickness. An integral operating finger tab 140 extends generally perpendicularly from the thicker annular wall portion at one end of the portion 130 of reduced thickness.

The finger tabs 100 and 140 are provided with roughened strips 142 on their outer opposite faces, shown only in FIGS. 5, 6, and 7., to facilitate their manipulation by the user of the catheter.

Two tubes 150 and 160 extend away from the wall 110, one 150 for oxygen and one 160 for suction. The two tubes 150 and 160 communicate with the inside of the body 40 through holes 152 and 162 in the rear wall 110. The rear wall 110 also has two holes 170 and 180 located on the same circumference as the two tubes 150 and 160, and a central opening 190. A small integral tab 200 having a notch 210 extends part way across the opening 190.

When the two bodies 30 and 40 are put together, the thin annular wall 122 of the body 40 fits snugly into the opening in body 30, and the leading end 212 butts up against the ledge 74. Similarly, the leading end 214 of body 30 butts up against ledge 216 where wall 122 meets wall 124 of the body 40. Also, the inner ends 51 and 61 of tubes 50 and 60 form a tight fit against the inner surface 112 of rear wall 110 of body 40 to provide an essentially leak proof coupling between body 30 and body 40. When the bodies 30 and 40 are put together, the finger tab 100 slips over the rim 132, and the notch 102 in the lower surface thereof engages and locks in on the rim.

The two bodies 30 and 40 are held together securely and tightly by means of a helical spring 218 which is secured at its ends in the notches 92 and 210 in the tabs 90 and 200. In attaching the spring 218, with the two bodies 30 and 40 loosely coupled together, one end of the spring is shaped like a hook and is secured to notch 92, and, with the other end grasped by a hooked instrument, the spring is rotated to bias it, and then its other end, which is also shaped like a hook, is set in notch 210 in tab 200, and the bodies are locked together. The spring holds bodies 30 and 40 tightly together with the inner portions 51 and 61 of tubes 50 and 60 snug against the inner surface 112 of end wall 110. The bias set into the spring serves to keep the bodies 30 and 40 rotated so that the finger tabs 100 and 140 are at their maximum distance apart. With this orientation of the bodies, the oxygen tube 60 is aligned with the oxygen feed tube 150 through its hole 152 in wall 110, and the suction tube 50 is aligned with hole 170 and the ambient atmosphere. When the tabs 100 and 140 are squeezed together, the suction tube 50 is aligned with suction tube 160 through its hole 162 in the wall 110, and the oxygen tube 60 is aligned with the hole 180 and the ambient atmosphere.

The tube 50 is connected by flexible plastic tubing 220 to a source of suction (not shown) and the tube 60 is similarly connected by tubing 230 to an oxygen source (not shown). The oxygen and suction tubes 150 and 160, on the patient side of the valve 20, are connected to the flexible tubes 240 and 250, rerspectively, which are coupled to the tubes 150 and 160. The oxygen tube 240 is of smaller diameter than the suction tube 250. The tubes 240 and 250 are manufactured as a single unit, and they preferably have generally semicircular cross-sections with the flat portions thereof adjacent to each other as seen in FIG. 3. Tubes 150 and 160 are similarly semicircular in cross section.

The tubes 240 and 250 are separated by a small amount at the valve ends to permit them to be handled and secured to the valve tubes 150 and 160. The unitary assembly of flexible tube-s 240 and 250 is provided with well-defined grooves 268 between them as seen in FIGS. 1 and 6 and it is manufactured so that there is a natural curvature built into it.

When the catheter 10 is used, both the built-in curvature and the difference in the diameters of the tubes 240 and 250 combine to impart controllability of the assembly by the operator and it permits easy buidance of the patient ends of the tubes into the throat and lungs. In addition, as the tubes are moved and rotated, the grooves 260 act as a rake and loosen mucus which can be removed by suction.

To insure proper coupling of the oxygen tube 240 to the oxygen line of the valve 20 and the suction tube 250 to the suction line of the valve, the flexible tubes 240 and 250 are coupled to the valve 20 through an adapter 310 (FIG. 10) which is described and claimed in co-pending application Ser. No. 270,057 filed Nov. 14, 1988 which is incorporated herein by reference. The adapter 310 comprises a rigid plastic body having two through holes 320 and 330 and has front surface 340 and a rear surface 350. The holes 320 and 330 are shaped and dimensioned so that when the adapter is coupled to rigid tubes 150 and 160 on the patient side of the valve mechanism 20, hole 320 forms a tight fit with tube 160 and hole 330 forms a tight fit with tube 150.

In preferred normal use of the valve 20, the finger tabs 100 and 140 are apart and all of the associated parts are arranged so that oxygen flows from the oxygen source, through tube 230, valve tubes 60 and 150 and lumen tube 240 and into the patient. At the same time, the suction source is coupled through tube 50 to the valve hole 170 to the atmosphere. After oxygen has been administered for a desired period of time, the tabs 100 and 140 are pressed together to align the suction tubes 50 and 160 to flexible tube 250 so that suction is administered and the oxygen source is connected to valve hole 180 to the atmosphere. After a time, the finger tabs 100 and 140 are released and suction is discontinued and oxygen is applied again.

It is noted that in use of the entire apparatus of the invention, the tube 60 of the valve 20 can be connected either to a source of oxygen or, if desired it may be connected to a source of irrigating fluid to introduce a quantity of saline or the like for lavage and then oxygen is reapplied to deliver the saline to the patient.

In another mode of using the above-described apparatus, with the two catheter tubes not used for suction or oxygen, the tubes are pulled back into the T connector and the valve 20 is operated to apply suction thereto and this suctions mucus out of the T connector.

According to the invention, in order to render the system a closed system wherein the patient can be isolated from the valve 20 and cannot lose oxygen through the tubes 240 and 250. Valve 20 is constructed so that the entrance openings inside the valve to rigid tubes 150 and 160 and their attached flexible tubes 240 and 250 are alternately blocked off from the patient as suction and oxygen are applied to the patient.

Figure 11:
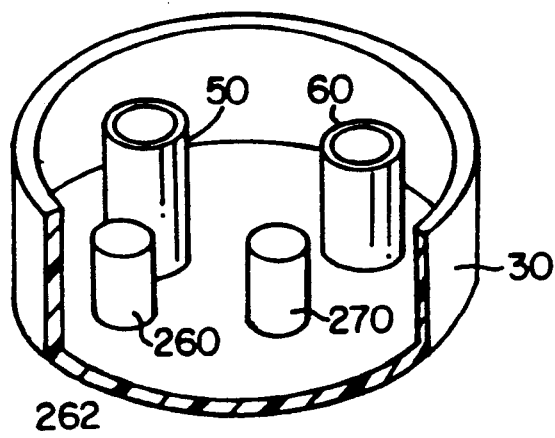
FIG. 11 is a perspective view of a modification of the valve of the invention.

According to the invention, referring to FIG. 11, this is achieved by providing a first solid boss or cylinder 260 on the inner surface 262 of the wall of valve portion 30 and positioned just beneath the tube 60. A similar second solid boss or cylinder 270 is provided on the surface 262 just beneath the tube 50. The two bosses are of such a length, like tubes 50 and 60, chat they contact and form a tight fit against the inner surface 112 of valve portion 40 when the two parts 30 and 40 of the valve 20 are assembled. The bosses 260 and 270 are positioned so that, when the source of oxygen is connected through tube 60, tube 150 and tube 240 to the patient and the suction tube is coupled to the opening to the atmosphere, boss 260 blocks the opening to tube 160 and to the lumen 250 to the patient so that the patient cannot breathe into the valve through this lumen.

Similarly, when the suction lines are aligned and the patient is being suctioned, the source of oxygen is aligned with the opening to the atmosphere and the second boss 270 blocks the opening into tube 150 and to the oxygen lumen 240 to the patient. Thus the patient cannot breathe into or from the valve 20 through the oxygem lumen.

Thus, the bosses 260 and 270 operate to provide a closed system as far as the patient is concerned and the lumens 240 and 250 to the patient are alternately blocked from the valve 20 as the patient is alternately oxygenated and suctioned. This prevents the patient's lungs from losing oxygen through the valve 20.

Thus, in using the apparatus of FIG. 1 with the valve 20 containing the bosses 260 and 270, with oxygen flowing into the patient through the coupling member 24 when the tubes 240 and 250 are introduced into the patient and oxygen is administered, the volume of oxygen in the patient's lungs is increased over a base level. Then when suction is applied for a short period of time as required, although some oxygen may be sucked out, the level remains at about the safe base level. In addition, when suction is applied, since the oxygen line through the valve is blocked by a boss, oxygen cannot escape from the lungs through the valve. Similarly, when oxygen is applied, the suction tube 250 is blocked by its boss in the valve and oxygen cannot be lost by the patient through the tube 250 and valve 20.

In order to prevent the catheter assembly from being withdrawn entirely from the T-connector 24 as it is being withdrawn from a patient, a flexible cord 282 is secured between the rear end 34 of connector 24 and the adapter 31. The cord 282 permits the catheter assembly to be inserted into the patient but when the assembly is withdrawn, it limits the extent to which it can be withdrawn and thus prevents it from being removed from the connector 24.

In the apparatus of the invention, in addition to a cleaning sponge or in place of a sponge, referring to FIG. 5, the rear chamber 24B of the T connector may be provided with a sleeve 353 having front and rear transverse walls 355 and 357 which have central openings 359 and 361 through which the double lumen catheter unit 22 passes in use. According to this aspect of the invention, the openings 359 and 361 have a shape like the lumen unit 22 as seen in FIG. 3 and these openings are dimensionsed so that when the lumen unit is withdrawn after use, the walls 355 and 357, which define the openings 359 and 361, scrape mucus from the lumen tubes and thus clean then.

It is noted that the catheter tubes 240 and 250 may be irrigated by withdrawing them into the cover 96, out of the rear end 34 of the T connector, removing the valve 20 from the connector 310 and coupling a source of irrigating fluid to one inlet to the connector 310 and a source of suction to the other inlet. Irrigating fluid flows down one catheter tube and then the suction draws it through the other tube.

What is claimed is:

1. An oxygen-suction catheter assembly including
a first hollow tubular portion comprising a front chamber for insertion into the mouth of a patient,
a second hollow tubular portion coupled to said first tubular portion and comprising a rear chamber for coupling patient treatment means into said first tubular portion and into a patient,
a third tubular portion coupled to said first tubular portion,
flexible tube means slidably coupled to said second hollow tubular portion for insertion through said second hollow tubular portion and said first hollow tubular portion into a patient,
a wall between said second tubular portion and said first tubular portion and having an aperture for permitting said flexible tube means to pass therethrough,
means adjacent to said wall for blocking and blocking said aperture,
said blocking and unblocking means having a first unblocked position when said flexible tube means is inserted through said aperture and into a patient and a second blocked position when said flexible tube means is withdrawn from a patient into said rear chamber, and
cleaning means in said rear chamber for cleaning said flexible tube means as it is withdrawn from a patient.

2. The apparatus defined in claim 1 wherein said cleaning means is a sponge which has a through hole through which flexible tube means is slid.

3. The apparatus defined in claim 2 wherein said through-hole has a cross-sectional shape comparable to the cross-sectional shape of said flexible tube.

4. The apparatus defined in claim 1 and including a sleeve positioned between said wall and said cleaning means, said cleaning means comprising a sponge.

5. The apparatus defined in claim 1 wherein said blocking and unblocking means comprising a slidable solid plate having an aperture, said solid plate being slid from a first position in which said plate aperture is in alignment with said wall aperture, and a second position in which said plate aperture is out of alignment with said wall aperture.

6. The apparatus defined in claim 1 wherein said first, second and third tubular portions form a T-shaped structure and said first and second portions are generally horizontal and aligned with each other and said third portion extends at an angle to said first and second portions.

7. The apparatus defined in claim 1 wherein said second tubular portion has an open end remote from said wall and including a removable cap coupled to said open end of said second tubular portion.

8. The apparatus defined in claim 1 and including first and second tubes secured to said rear chamber and accessible outside said rear chamber whereby said first tube can be connected to a source of suction and said second tube can be open as a vent.

9. The apparatus defined in claim 1 wherein said flexible tube means has a patient end which is inserted into said first tubular portion and a remote end,
a valve secured to said remote end of said flexible tube means,
said valve including a first inlet pipe for receiving oxygen and a first outlet pipe for receiving oxygen from said first inlet pipe and coupled to said flexible tube means, said valve also including a second inlet pipe for receiving suction and a second outlet pipe for receiving suction from said second inlet pipe and coupled to said flexible tube means,
holes in said valve for venting suction and oxygen to air when one or the other is not connected to said first or second outlet pipes, and
auxiliary means in said valve for blocking said first outlet pipe when said second outlet pipe is receiving suction and for blocking said second outlet pipe when said first outlet pipe is receiving oxygen whereby a patient will not lose oxygen during a suctioning operation.

10. The apparatus defined in claim 9 and including a protective sleeve secured between said second tubular portion and said valve and enclosing said flexible tube means.

11. The apparatus defined in claim 1 and including securing means coupled between said rear chamber and said flexible tube means whereby said flexible tube means is prevented from being removed from said rear chamber.

12. A catheter assembly comprising:
a hollow T-shaped member including a cross member and an arm extending therefrom, said cross member having a front end adapted to be inserted into a patient and a rear end,
a wall extending across said cross member and closing off said rear end of said connector from said arm and said front end of said connector,
means operable by an operator to open said wall, and second means in said rear end of said cross member for permitting a portion of a catheter to pass therethrough and to be cleaned thereby.

13. The apparatus defined in claim 12 wherein said second means is a sponge.

14. The apparatus defined in claim 13 wherein said sponge has means for permitting a catheter to pass through it.

15. The apparatus defined in claim 12 wherein said means comprises a plate in said wall adapted to be moved to provide an opening in said wall.

16. The apparatus defined in claim 12 wherein said means is a slide in said wall adapted to be moved to provide an opening in said wall.

* * * * *